US005625426A

United States Patent [19]

Liu

[11] Patent Number: 5,625,426

[45] Date of Patent: Apr. 29, 1997

[54] VISION CORRECTING DEVICE

[76] Inventor: Hsing Chuan Liu, No. 168, Taichung Road, Taichung City, Taiwan

[21] Appl. No.: 603,946

[22] Filed: Feb. 20, 1996

[51] Int. Cl.⁶ .................................. G02C 1/00; A61F 5/00

[52] U.S. Cl. ......................... 351/158; 351/41; 606/204.25

[58] Field of Search ..................... 351/41, 158; 606/201, 606/204.25; 261/24, 30, 38

[56] References Cited

U.S. PATENT DOCUMENTS 2,690,173 9/1954 Seeger et al. ....................... 606/204.25

*Primary Examiner*—Huy Mai

*Attorney, Agent, or Firm*—Pro-Techtor International

[57] ABSTRACT

A vision correcting device comprises an eye shield, an air tube fastened at one end thereof with the eye shield, and a pressure apparatus fastened with another end of the air tube. The pressure apparatus comprises a motor, a speed-changing mechanism driven by the motor, an eccentric wheel actuated by the speed-changing mechanism, a roller, a push rod, and an air sac. When the eccentric wheel is actuated to turn clockwise, the push rod is actuated to cause the air sac to contract rapidly and relax slowly so as to bring about a positive pressure in the shield for the treatment of myopia. When the eccentric wheel is actuated to turn counterclockwise, the push rod is actuated to cause the air sac to contract slowly and relax rapidly so as to bring about a negative pressure in the shield for the treatment of hyperopia.

7 Claims, 7 Drawing Sheets

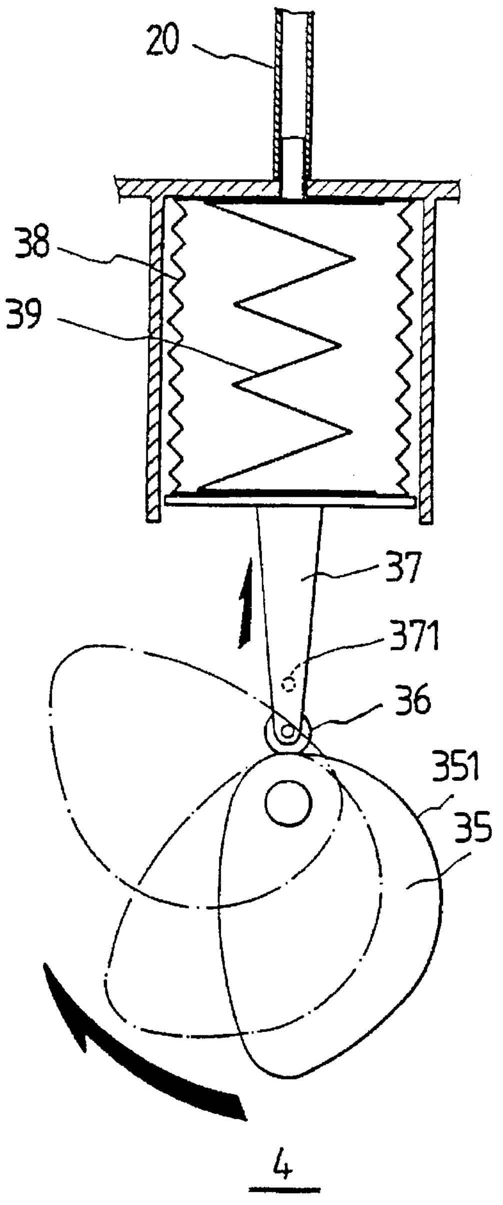
FIG, 4
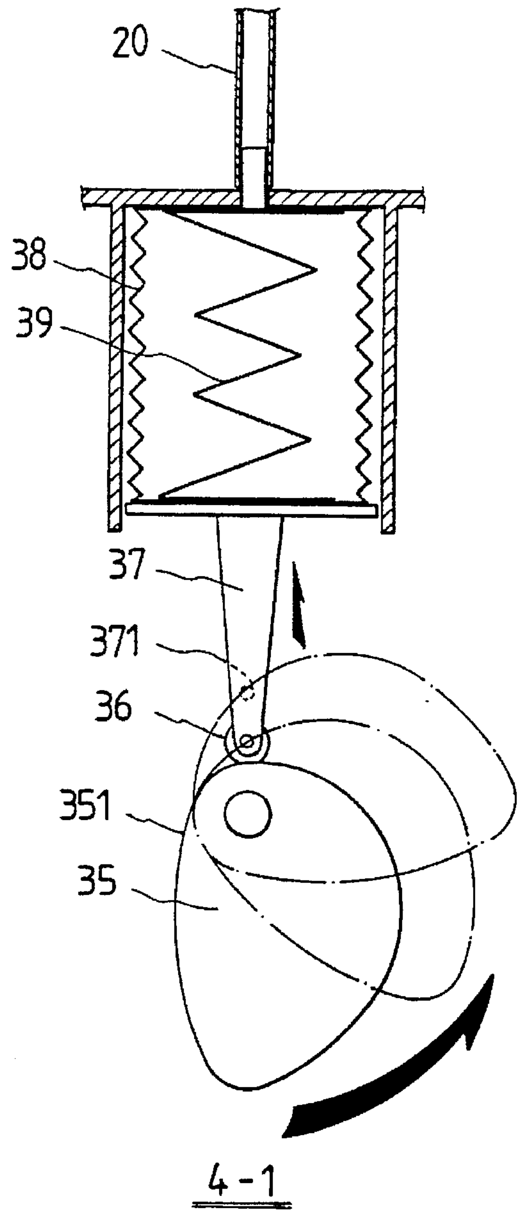
FIG, 5

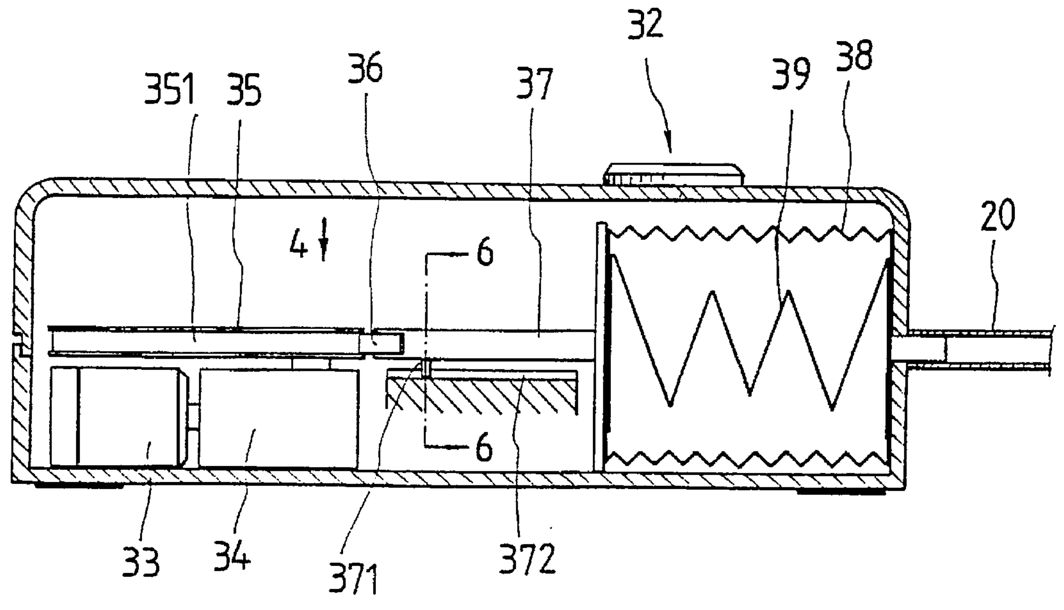
FIG, 3
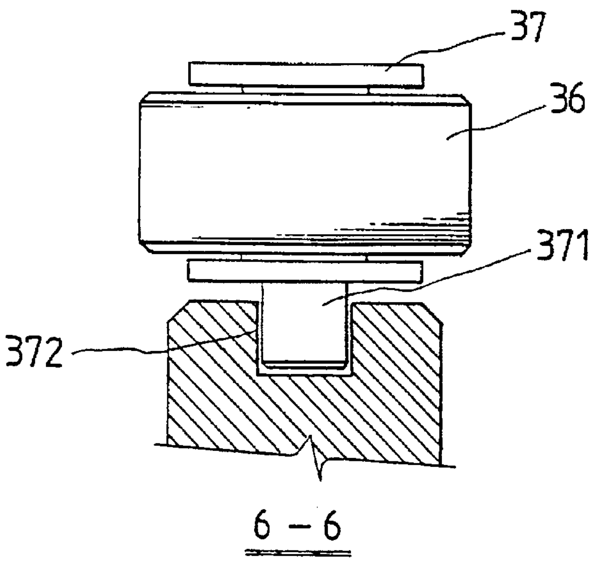
FIG, 6

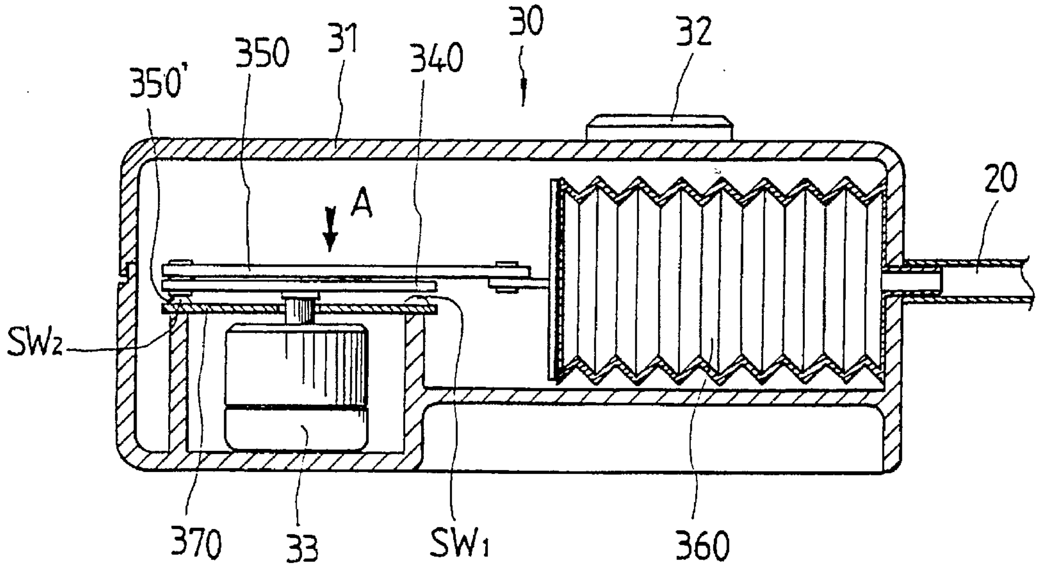
FIG, 7
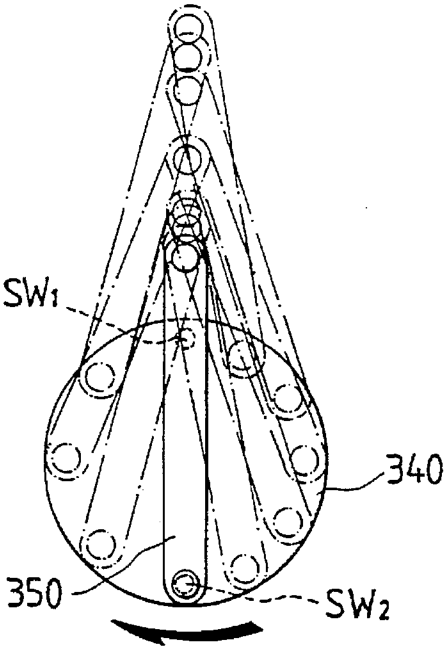
FIG, 8
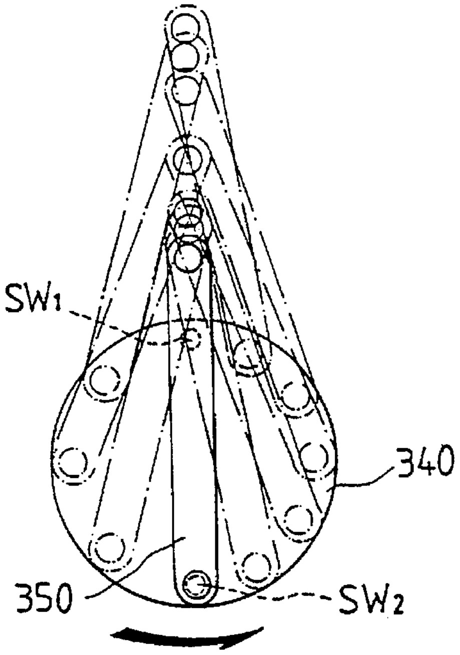
FIG, 9

VISION CORRECTING DEVICE

FIELD OF THE INVENTION

The present invention relates generally to a vision correcting device, and more particularly to a device for correcting hyperopia or myopia.

BACKGROUND OF THE INVENTION

As shown in FIG. 1, a vision correcting device of the prior art is intended for use in correcting the farsightedness or the nearsightedness and is composed of a farsightedness or the nearsightedness and is composed of a shield 1, a gas tube 2, and a pressure apparatus 3. The pressure apparatus 3 is a spherical air sac of a plastic material. When the pressure apparatus 3 is squeezed with hand, an increase in the air pressure inside the shield 1 is brought about so as to cause a reduction in the curvature of the eye lens of a person under treatment for myopia. On the other hand, when the pressure apparatus 3 is relieved of the external force exerting thereon, a reduction in the air pressure inside the shield 1 is brought about so as to cause an increase in the curvature of the eye lens of a person under treatment for hyperopia. Such a manually-operated pressure apparatus 3 as described above is limited in design in that it does not provide the shield 1 with the desired air pressure with precision, and that it is difficult for a person, especially a youngster, to operate correctly and precisely.

SUMMARY OF THE INVENTION

It is therefore the primary objective of the present invention to provide a vision correcting device with a pressure apparatus capable of adjusting the air pressure of the vision correcting device with precision. The vision correcting device of the present invention comprises a shield, an air tube, and a pressure apparatus which is provided with a speed-changing mechanism driven by a motor. The pressure apparatus is further provided with an eccentric wheel capable of being actuated by the speed-changing mechanism. An increase or decrease in the air pressure inside the shield is regulated with precision by an air sac capable of being caused by the rotational motion of the eccentric wheel to expand or contract.

BRIEF DESCRIPTION OF THE DRAWINGS

FIG. 3 shows a partial sectional view of the vision correcting device of the present invention.

FIG. 4 shows a schematic view of the pressure apparatus of the vision correcting device of the present invention at work.

FIG. 5 shows another schematic view of the pressure apparatus of the vision correcting device of the present invention at work.

FIG. 6 shows a sectional view of a push rod of the vision correcting device of the present invention.

FIG. 7 shows a plan sectional view of the pressure apparatus of a second preferred embodiment of the present invention.

FIG. 8 shows a schematic view of the pressure apparatus of the second preferred embodiment of the present invention at work.

FIG. 9 shows another schematic view of the pressure apparatus of the second preferred embodiment of the present invention at work.

DETAILED DESCRIPTION OF THE INVENTION

Figure 1:
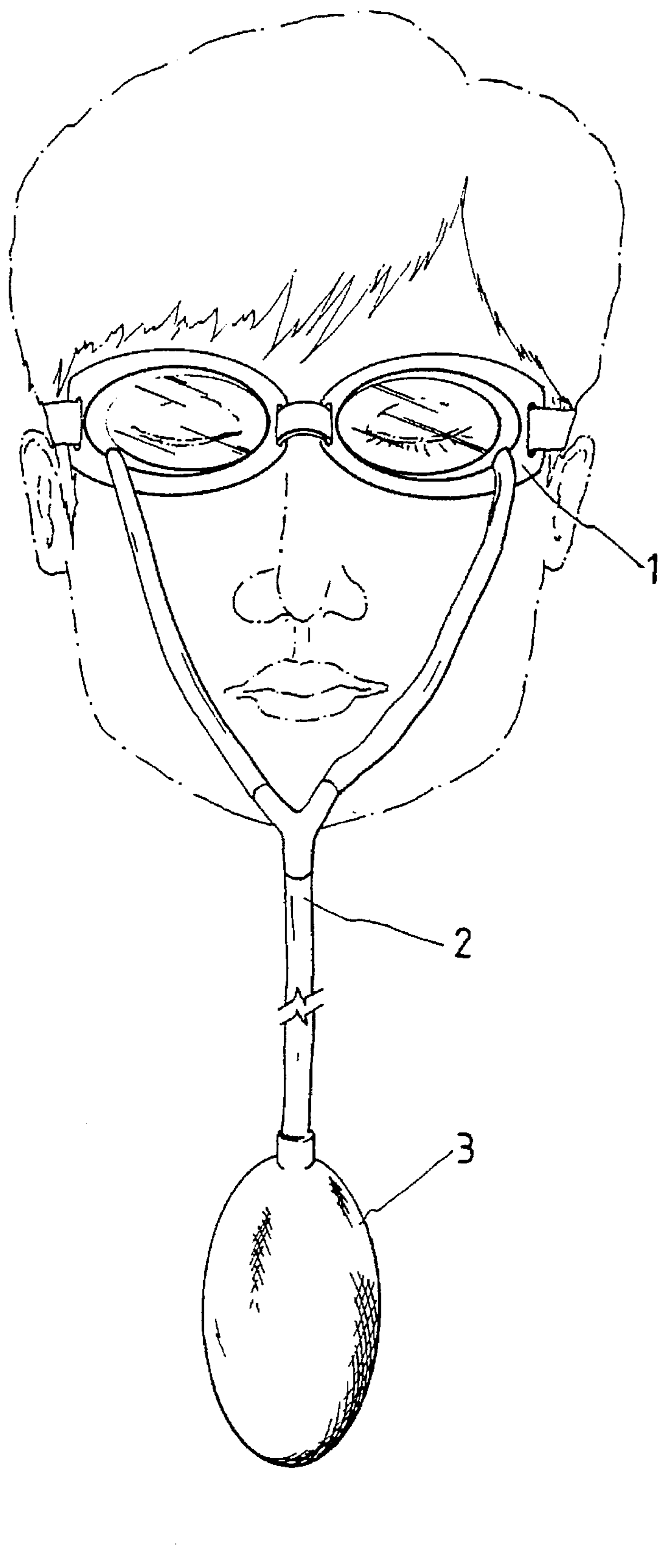
FIG. 1 shows a schematic view of a vision correcting device of the prior art at work.
Figure 2:
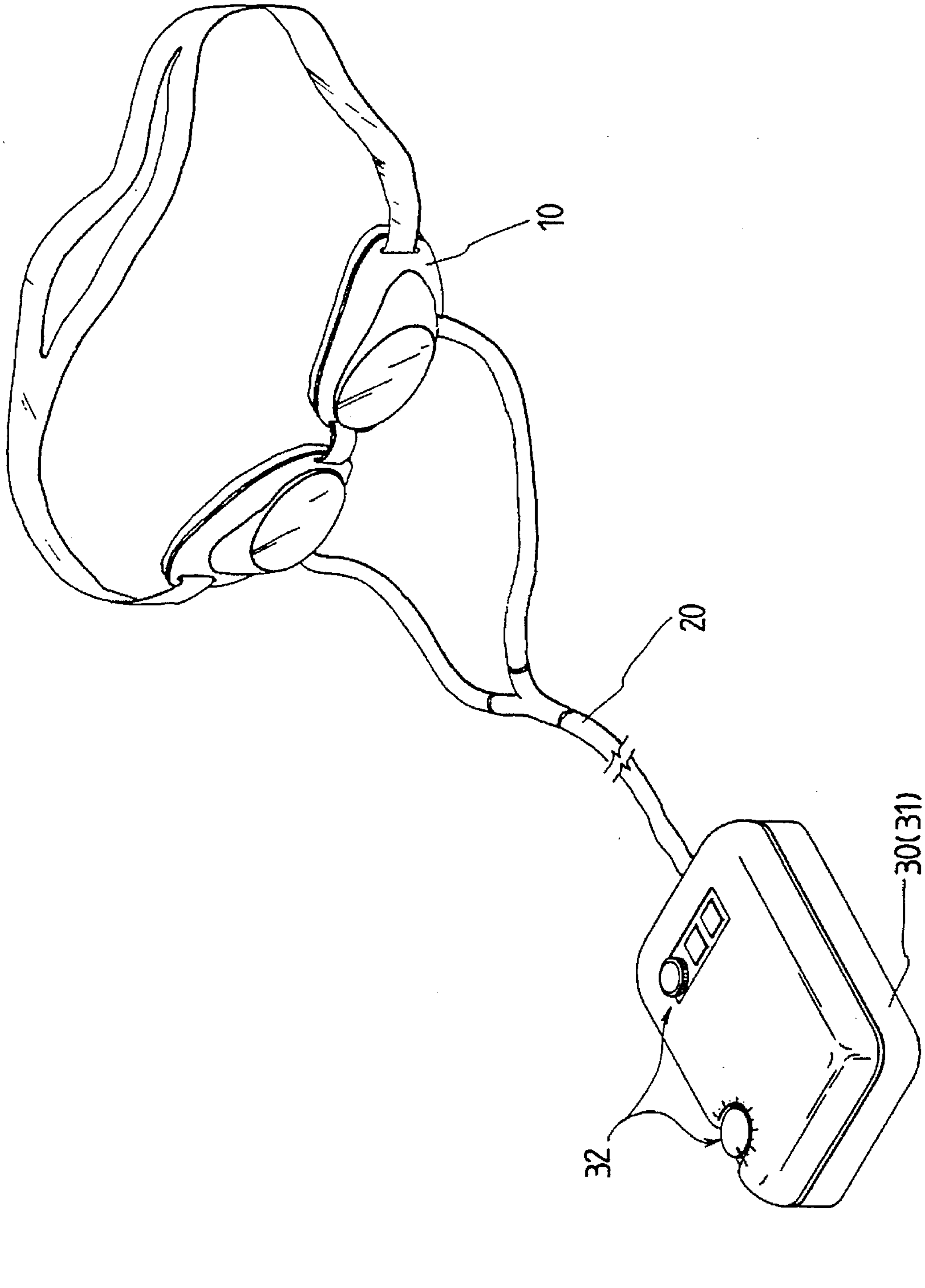
FIG. 2 shows a perspective view of a vision correcting device of the present invention.

As shown in FIGS. 2 and 3, a vision correcting device embodied in the present invention comprises a shield, and air tube 20, and a pressure apparatus 30.

The shield 10 has two units fastened with the eyes of a person under treatment for hyperopia or myopia.

The air tube 20 is fastened at one end thereof with the shield 10 and at another end thereof with the pressure apparatus 3.

The pressure apparatus 30 has a housing 31 provided with a plurality of control buttons 32. The housing 31 is provided therein with a hollow interior in which a motor 33, a speed-changing mechanism 34, an eccentric wheel 35, a roller 36, a push rod 37, an air sac 38, and a spring 39 are disposed. The speed-changing mechanism 34 is driven by the motor 33 so as to actuate the eccentric wheel 35, which has a wheel surface 351 making contact with the roller 36. When the eccentric wheel 35 is actuated to turn clockwise as shown in FIG. 4, the push rod 37 which is fastened at one end thereof, with the roller 36 is actuated to cause the air sac 38 to contract rapidly and relax slowly so as to bring about a positive air pressure in the shield 10 via the air tube 20 for the treatment of myopia. On the other hand, when the eccentric wheel 35 is driven by the motor 35 to turn counterclockwise as shown in FIG. 5, the air sac 38 is caused by the push rod 37 to contract slowly and relax rapidly so as to bring about a negative air pressure in the shield 10 via the air tube 20 for the treatment of hyperopia. The air sac 38 is provided therein with a spring 39 to faxilitate the contraction and the relaxation of the air sac 38. The push rod 37 is caused to move back and forth by the motion of the eccentric wheel 35, as shown in FIG. 6. The push rod 37 is provided at the bottom end thereof with a guide column 371, which is received movably in the slide slot 372 at the time when the push rod 37 is caused to move by the eccentric wheel 35. In other words, the push rod 37 is prevented from moving aside by means of the guide column 371 and the slide slot 372 so as to ensure that the air sac 38 is caused by the push rod 37 to contract and relax with precision, as shown in FIG. 6.

As shown in FIGS. 7, 8 and 9, the pressure apparatus 30 of the second preferred embodiment of the present invention comprises a housing 31 provided on the surface thereof with a plurality of control buttons 32, which are respectively an ON-OFF switch button, a forward rotation control button, a reverse rotation control button, a speed adjustment control button, and a time adjustment control button. The housing 31 houses therein a motor 33 for driving a speed-changing mechanism 34. The speed of motor 33 can be adjusted variably by the speed adjustment control button. The forward rotation and the reverse rotation of the motor 33 are regulated respectively by the forward rotation control button and the reverse rotation control button. The ON-OFF switch button is used to start and stop the motor 33, which is used to drive a rotary wheel 340 pivoted with a connection rod 350. The connection rod 350 is fastened with an air sac 360. Located between the rotary wheel 340 and the motor 33 is a control panel 370 which is provided with two touch-control switch SW1 and SW2, which are opposite to each other. When the rotary wheel 340 is driven by the motor 33 to turn clockwise, the touch-control switch SW1 is first pressed by a pivoting point 350' of the connection rod 350 and is intended to regulate the variable acceleration of the motor 33 so as to bring about an instant increase in the revolving speed of the motor 33. As a result, the speed at which the connection rod 350 is pulled is accelerated. When the touch-control switch SW2 is pressed by the pivoting point 350', the variable deceleration of the motor 33 is brought about so as to result in an instant decrease in the revolving speed of the motor 33. As a result, the speed at which the connection rod 350 is pushed is reduced. The connection rod 350 is therefore capalbe of acting on the air sac 360 in such a manner that the air sac 360 is caused to contract rapidly and to relax slowly for treating the myopia. On the other hand, when the motor 33 is caused to turn counterclockwise, the connection rod 350 is caused to act on the air sac 360 in such a manner that the air sac 360 is caused to contract slowly and to relax rapidly for treating the hyperopia.

Figures 10, 10A:
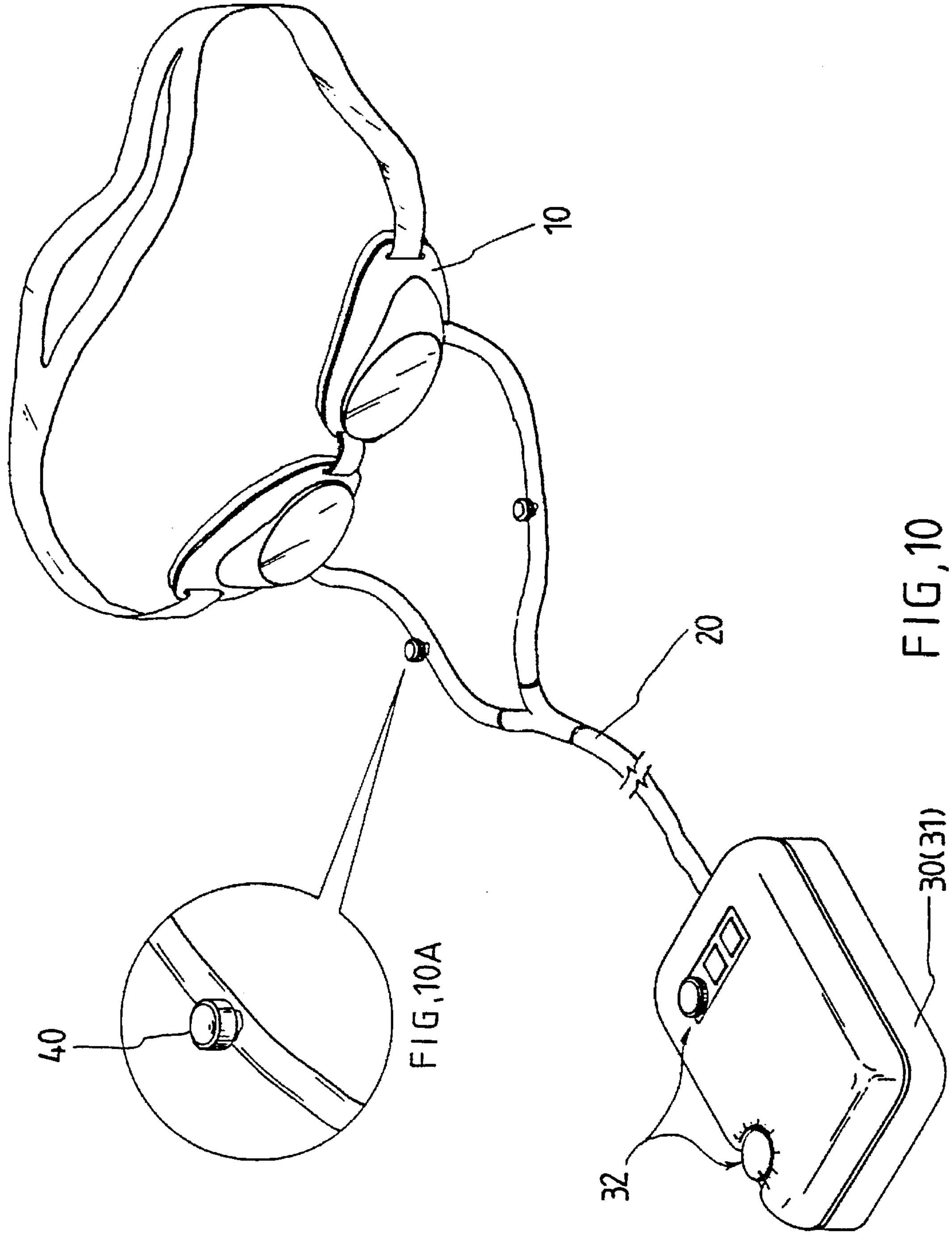
FIG. 10 shows a schematic view of the air tube of the second preferred embodiment of the present invention.

As shown in FIG. 10, the air tube 20 of another preferred embodiment of the present invention is provided with two pressure adjustment buttons 40 for adjusting the air pressure in the left side or the right side of the shield 10.

Figure 11:
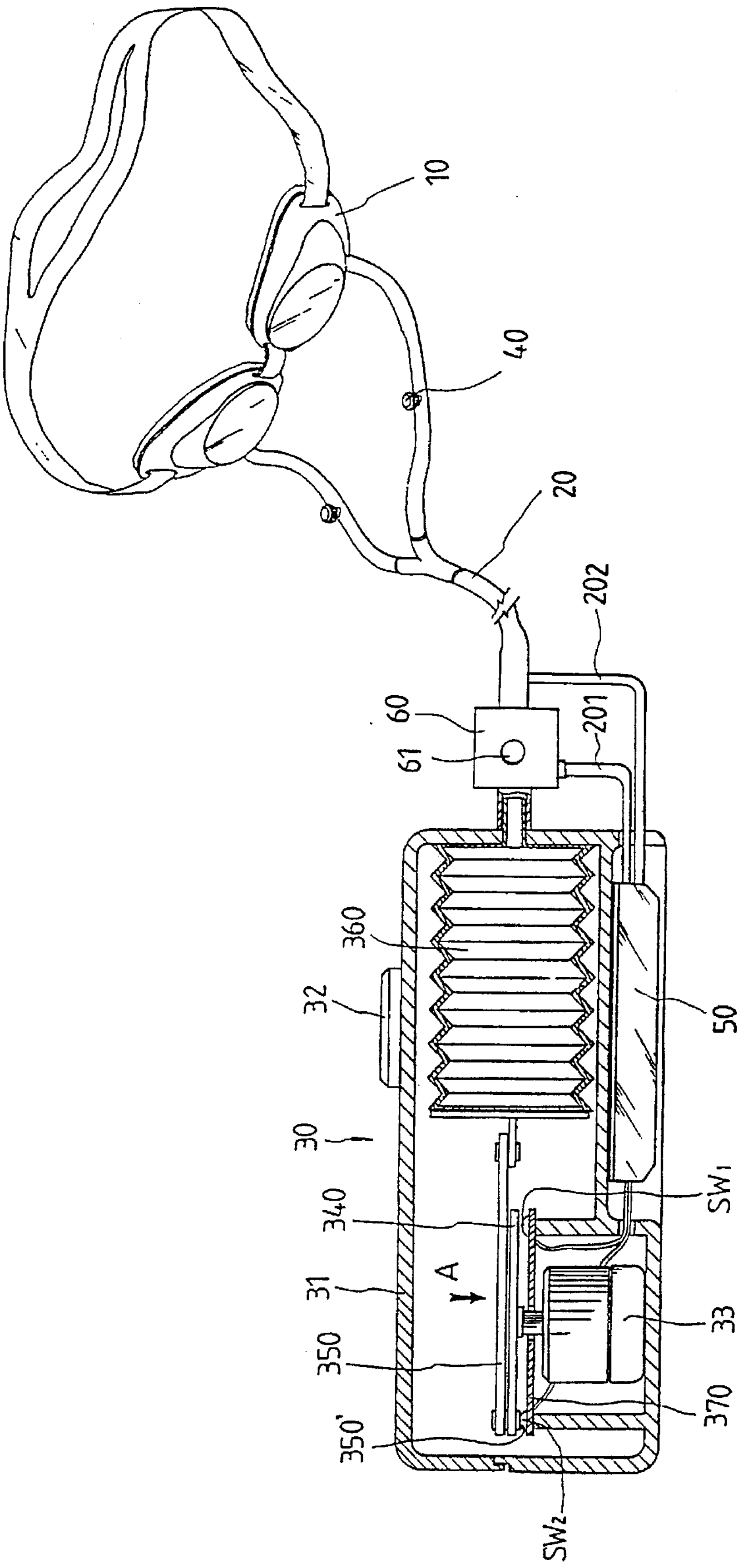
FIG. 11 shows a schematic view of a third preferred embodiment of the present invention.

As shown in FIG. 11, a vision correction device of the third preferred embodiment of the present invention comprises the pressure apparatus 30 provided with a control device 50 which is connected with an electromagnetic pressure relief valve 60 by an air duct 201 and is further connected with the air tube 20 by another air duct 202. When the motor 33 is started to pull the air sac 360 from the connection rod 350 to a full extent so as to bring about the positive pressure to treat the myopia, the control device 50 causes the air to pass the electromagnetic pressure relief valve 60 (the opening 61 of the electromagnetic pressure relief valve 60 is closed) so as to guide the air pressure to the shield 10. When the air sac 360 is pulled backwards by the connection rod 350 to bring about the negative pressure, the control device 50 cause the opening 61 of the electromagnetic pressure relief valve 60 to open slightly to allow the atmospheric air to enter such that the shield 10 is devoid of the negative pressure for treating the hyperopia. The control device 50 is triggered by the detected pressure (positive and negative) so as to actuate the electromagnetic pressure relief valve 60 to discharge via the opening 61 the excess air to correct the excessive positive pressure or the excessive negative pressure. In other words, the vision correcting device of the present invention is provided with the control device 50 and the electromagnetic pressure relief valve 60 for regulating the precise positive pressure and the precise negative pressure.

The embodiments of the present invention described above are to be regarded in all respects as being merely illustrative and not restrictive. Accordingly, the present invention may be embodied in other specific forms without deviating from the spirit thereof. The present invention is therefore to be limited only by the scopes of the following appended claims.

What is claimed is:

1. A vision correcting device, which comprises:

an eye shield for fitting over both eyes of a person;

an air tube fastened at one end thereof with said eye shield; and a pressure apparatus fastened with another end of said air tube for adjusting air pressure inside said eye shield for the treatment of myopia or hyperopia of said person;

Wherein said pressure apparatus has a housing provided with a plurality of control buttons, said housing further provided therein with a hollow interior for housing a motor, a speed-changing mechanism, an eccentric wheel, a roller, a push rod, and an air sac, said motor intended for use in driving said speed-changing mechanism to actuate said eccentric wheel making contact with said roller which is fastened with said push rod capable of causing said air sac to contract rapidly and relax slowly so as to bring about a positive air pressure in said shield via said air tube when said eccentric wheel is actuated by said speed-changing mechanism to turn clockwise, said push rod further capable of causing said air sac to contract slowly and relax rapidly so as to bring about a negative air pressure in said shield via said air tube when said eccentric wheel is actuated by said speed-changing mechanism to turn counterclockwise.

2. The vision correcting device as defined in claim 1, wherein said air sac is provided with a biasing means to facilitate the contracting and the relaxing of said air sac.

3. The vision correcting device as defined in claim 1, therein said air tube is provided with two pressure adjustment buttons for regulating air pressure in said shield.

4. The vision correcting device as defined in claim 1, wherein said pressure apparatus is provided with a rotary wheel driven by a motor, said rotary wheel pivoted with a connection rod which is connected with an air sac, said pressure apparatus provided with a control panel located between said rotary wheel and said motor, said control panel provided thereof with two touch-control switches which are pressed by a pivoting point of said rotary wheel and said connection rod for regulating the revolving rate of said motor so as to control the action of said connection rod on said air sac to bring about a positive pressure or a negative pressure in said shield.

5. The vision correcting device as defined in claim 4, wherein said pivoting point is provided with a magnet for attracting said touch-control switches when said pivoting point is actuated by said rotary wheel.

6. The vision correcting device as defined in claim 1, wherein said air tube is provided with two pressure adjustment buttons for adjusting air pressure in said shield.

7. The vision correcting device as defined in claim 1, wherein said pressure apparatus is provided with a control device connected with an electromagnetic pressure relief valve via an air duct and with said air tube via another air duct; wherein said connection rod is actuated by said motor to pull said air sac to bring about a positive pressure for treating myopia; wherein said control device allows air to pass said electromagnetic pressure relief valve (with an opening of said electromagnetic pressure relief valve remaining closed) so as to guide air pressure to said shield; wherein said air sac is pulled backwards by said connection rod to bring about a negative pressure to actuate said control device to open said opening of said electromagnetic pressure relief valve to allow atmospheric air to enter so as to ensure that said shield is devoid of a negative pressure for treating hyperopia; and wherein said control device actuates said electromagnetic pressure relief valve to discharge via said opening the excess air to correct an excessive positive pressure or an excessive negative pressure.

* * * * *